US008206941B2

(12) United States Patent
Enderle et al.

(10) Patent No.: US 8,206,941 B2
(45) Date of Patent: Jun. 26, 2012

(54) THREE PART ASSAY FOR KINASE OR PHOSPHATASE ACTIVITY

(75) Inventors: Thilo Enderle, Rheinfelden (DE); Doris Roth, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 385 days.

(21) Appl. No.: 12/485,283

(22) Filed: Jun. 16, 2009

(65) Prior Publication Data
US 2009/0253150 A1 Oct. 8, 2009

Related U.S. Application Data

(63) Continuation of application No. 11/490,341, filed on Jul. 20, 2006, now abandoned.

(30) Foreign Application Priority Data

Jul. 29, 2005 (WO) .................. PCT/EP2005/053720
Aug. 4, 2005 (EP) ..................................... 05107192

(51) Int. Cl.
*C12Q 1/00* (2006.01)
*C12Q 1/48* (2006.01)
*C12Q 1/42* (2006.01)
*G01N 21/00* (2006.01)

(52) U.S. Cl. .................. 435/15; 435/4; 435/21; 436/164

(58) Field of Classification Search .................... None
See application file for complete search history.

(56) References Cited

U.S. PATENT DOCUMENTS 6,203,994 B1 * 3/2001 Epps et al. ..................... 435/7.1
6,972,198 B2 * 12/2005 Craig et al. ................... 436/164

FOREIGN PATENT DOCUMENTS

| EP | 1 156 329 | 11/2001 |
| WO | WO 00/75167 | 12/2000 |
| WO | WO 02/41001 | 5/2002 |
| WO | WO 02/102834 | 12/2002 |

OTHER PUBLICATIONS

Olive et al. Quantitative Methods for Analysis of Protein Phosphorylation in Drug Development; Expert Reviews of Proteomics; vol. 1, No. 3 (2004) pp. 89-103.*

* cited by examiner

*Primary Examiner* — Rebecca Prouty
*Assistant Examiner* — Paul Martin
(74) *Attorney, Agent, or Firm* — George W. Johnston; Dennis P. Tramaloni; Brian C. Remy

(57) ABSTRACT

The present invention relates to a method of determining kinase or phosphatase activity based on a three parts system. The method comprises contacting a binding partner which can bind phosphorylated peptides, a detection molecule and a substrate peptide. Determination of activities is achieved by measuring energy transfer between an energy donor and an energy acceptor that are present on the detection molecule and the substrate molecule.

6 Claims, 10 Drawing Sheets

Figute 7 continued
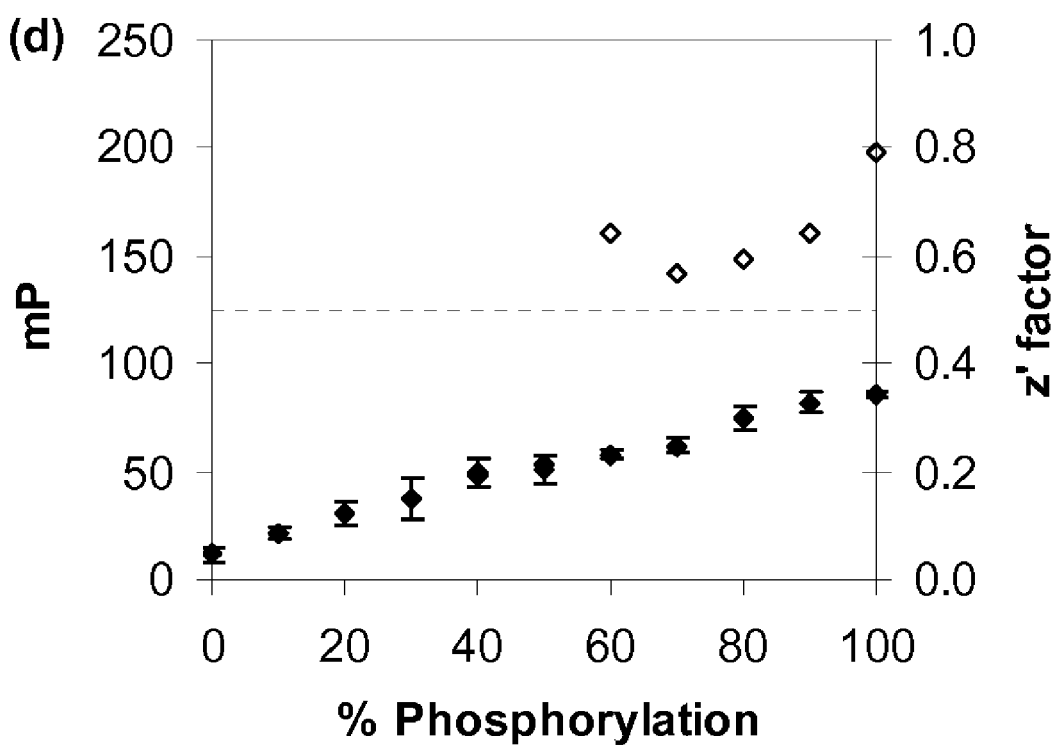

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr His Gly His Ser Met Ser Ala Pro Gly Val Ser Thr Ala Cys
1               5                   10                  15
```

THREE PART ASSAY FOR KINASE OR PHOSPHATASE ACTIVITY

PRIORITY TO RELATED APPLICATIONS

This application is a Continuation of U.S. Patent application Ser. No. 11/490,341, filed on Jul. 20, 2006, now abandoned, and claims the benefit of PCT/EP2005/053720, filed on Jul. 29, 2005 and European Application No. 05107192.6, filed Aug. 4, 2005, which are hereby incorporated by reference in their entirety.

Sequence Listing

The instant application contains a Sequence Listing which has been submitted in ASCII format via EFS-Web and is hereby incorporated by reference in its entirety. Said ASCII copy, created on Jan. 25, 2012, is named 23240US1.txt and is 657 bytes in size.

BACKGROUND OF THE INVENTION

The physiological modification of molecules and supramolecular assemblies plays a major role in the structure and regulation of biological systems. These modifications may include phosphorylation, cyclization, glycosylation, acylation, and/or sulfation, among others, and the modified molecules may include polypeptides, nucleic acids, and/or lipids, among others. The importance of modifications is particularly evident in the cell-signaling pathway, in which extracellular and intracellular substances related by phosphate modifications such as phosphorylation and cyclization influence the position, nature, and activity of cells.

Compounds which can interfere with phosphorylation or dephosphorylation catalysed by specific enzymes, or of specific substrates, are of interest since they may interfere with specific signaling events and thus be useful for treatment or prevention of diseases which occur through dysregulation of such pathways.

Therefore, it is of interest to develop methods of determining kinase or phosphatase activity for screening for compounds that can modulate specific signaling pathways.

EP1156329 discloses a method of determining kinase activity based on a system of two parts, the binding partner (BP) and the substrate molecule (A) which is converted (A*) or A->A*. In general, the binding partner is an entity that binds the enzyme product and can itself be attached to a solid phase e.g. a bead by any kind of interaction, covalent or non-covalent. For detection, a label (fluorophore, luminophore, acceptor or quencer) is attached to A or the BP. The list of detection methods includes intensity, polarization and energy transfer measurements.

WO00/75167 discloses a method of detecting addition or removal of a substrate group to or from a substrate which is also based on a system of two parts, the binding partner, which is preferably a macromolecule having entrapped metal ions, and a peptide A, wherein the conversion of phosphorylated to unphosphorylated peptide or vice versa is measured, e.g. by FRET (Fluorescence resonance energy transfer).

One drawback of the two parts systems is that for optimal energy transfer, for a given BP and A* ratio, a certain ratio of donor and acceptor is required. Thus, for optimal FRET generation, it may be necessary to titrate BP, A and A*.

However, the optimum ratios between BP, A and A* are generally influenced by the binding capacity of BP for A* and the respective binding constants on one hand, and also by the kinetic parameters of the enzyme reaction for the target of interest on the other hand. Therefore, the fixed ratio of BP, A and A* which is necessary for FRET optimization in a two parts system leads to a compromise in either assay signal and quality or enzyme kinetics and biological meaning of the results, i.e. in the worst case it may be impossible in a two parts system to achieve the optimum for all components: enzyme reaction for optimum kinetics, BP and A* for optimum binding of converted product, acceptor-donor for optimum FRET.

One embodiment of the two parts system disclosed in EP 1156329 and WO00/75167 comprises plastic beads that are doped with either luminophore or acceptor and a surface coating to bind the labeled A*. In other words IMAP™ beads with optical label in the core of the beads.

To achieve sufficient binding capacity the IMAP™ beads typically have a diameter of 100 nm or more. This is big compared to the energy transfer distance of a typical donor acceptor pair which is 3 to maximally 9 nm. As a consequence the energy transfer between a doped bead and a bound peptide is rather inefficient as there are many luminophores inside the bead which don't see a FRET partner but still contribute to assay background signal. This leads to a reduced dynamic range and decrease in sensitivity.

Therefore, there is a need to develop a more efficient method for determining kinase or phosphatase activity by energy transfer measurements between an energy donor and an energy acceptor

SUMMARY OF THE INVENTION

The present invention relates to a method of determining kinase or phosphatase activity comprising interacting a binding partner, a detection molecule and a substrate molecule. More specifically, the assay method of the present invention consists of three parts: (i) a "binding partner" (ii) a detection molecule which is labeled with donor or acceptor of a FRET pair (iii) a substrate molecule—a small molecule, peptide or protein—which is converted by the enzyme and thereby an amino acid (Ser, Thr, Tyr) is phosphorylated if the enzyme is a protein kinase. The same setup can be used for protein phosphatases where the respective amino acid is de-phosphorylated.

Thus, the present invention provides a method for determining kinase or phosphatase activity comprising interacting a binding partner, a detection molecule and a substrate peptide, wherein said detection molecule is labeled with an energy donor or acceptor and said substrate molecule is labeled with an energy donor, if the detection molecule is labeled with an energy acceptor, or with an energy acceptor, if the detection molecule is labeled with an energy donor, wherein said binding partner only binds phosphorylated substrate molecule, which method comprises the steps of: a) phosphorylating said substrate molecule with a kinase or dephosphorylating a phosphorylated substrate molecule with a phosphatase; and b) interacting (contacting) the substrate molecule obtained in step a) with said binding partner and said detection molecule; and c) determining kinase or phosphatase activity by measuring energy transfer from the energy donor to the energy acceptor of said substrate molecule and said detector molecule bound to said binding partner, wherein the energy donor has an emission lifetime of less than about 50 microseconds, preferably less than about 10 microseconds and more preferably less than about 5 microseconds.

Preferably, said binding partner are metal ions which are preferably associated with a solid phase, e.g. a bead, membrane, sample holder and surface of a microtiter plate. In a most preferred embodiment, said binding partner are metal ions on IMAP™ beads. IMAP™ beads may be obtained from Molecular Devices Corp. It has been shown that IMAP™ beads can be used as binding platform to bring two fluorophores close enough together for fluorescence resonance energy transfer (FRET) being thus a universal detection system for kinase assays and phosphatase assays.

In another preferred embodiment, the substrate molecule is a protein or a peptide.

DETAILED DESCRIPTION OF THE INVENTION

Definitions

Figure 1:
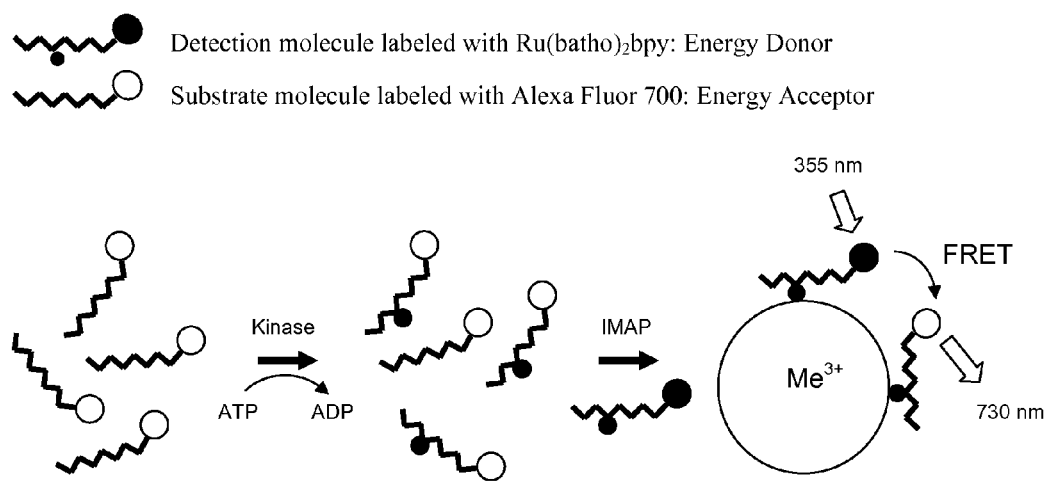
FIG. 1: Scheme of the kinase reaction using IMAP™ beads for Fast-TR FRET readout.

As used herein, "binding partner" refers to an entity (e.g. any molecule, for instance an antibody) that binds the enzyme product and can itself be attached to a solid phase e.g. a bead by any kind of interaction, covalent or non-covalent.

As used herein, "detection molecule" refers to a molecule which carries a label, e.g. a fluorescent label, that allows detection of the detection molecule, and which binds to the binding partner.

As used herein, "substrate molecule" refers to a small molecule, peptide or protein which is converted by the enzyme through an enzymatic reaction.

As used herein, "energy donor" refers to a fluorescent label which, upon excitation, can transfer its energy to the energy acceptor. All energy donors of a FRET point are included, preferably donors of TR-FRET and Fast-TR Fret. More preferably, the embodiments of the energy donor comprise lanthanide chelates and cryptates, along with Ru.

As used herein, "energy acceptor" refers to a molecule which can receive energy from the energy donor.]

As used herein, "kinase activity" refers to phosphorylation of a substrate by an enzyme (kinase)

As used herein, "phosphatase activity" refers to dephosphorylation of a substrate by an enzyme (phosphatase)

As used herein, "phosphorylated substrate molecule" refers to a small molecule, peptide or protein which is phosphorylated by the enzyme (kinase).

As used herein, "emission lifetime" refers to the average amount of time a fluorophore remains in the excited state following excitation.

As used herein "FRET pair" refers to the pair(ing) of an energy donor and an energy acceptor, wherein the FRET (fluorescence resource energy transfer) occurs between said energy donor and said energy acceptor.

All references cited herein, supra and infra, are hereby incorporated by reference in their entirety.

DETAILED DESCRIPTION

The present invention relates to a method of determining kinase or phosphatase activity comprising interacting a binding partner, a detection molecule and a substrate molecule.

The assay method of the present invention consists of three parts: (i) a "binding partner" (ii) a detection molecule which is labeled with donor or acceptor of a FRET pair (iii) a substrate molecule—a small molecule, peptide or protein—which is converted by the enzyme and thereby an amino acid (Ser, Thr, Tyr) is phosphorylated if the enzyme is a protein kinase. The same setup can be used for protein phosphatases where the respective amino acid is de-phosphorylated.

Thus, the present invention provides a method for determining kinase or phosphatase activity comprising interacting a binding partner, a detection molecule and a substrate peptide, wherein said detection molecule is labeled with an energy donor or acceptor and said substrate molecule is labeled with an energy donor, if the detection molecule is labeled with an energy acceptor, or with an energy acceptor, if the detection molecule is labeled with an energy donor, wherein said binding partner only binds phosphorylated substrate molecule, which method comprises the steps of: a) phosphorylating said substrate molecule with a kinase or dephosphorylating a phosphorylated substrate molecule with a phosphatase; and b) interacting the substrate molecule obtained in step a) with said binding partner and said detection molecule; and c) determining kinase or phosphatase activity by measuring energy transfer from the energy donor to the energy acceptor of said substrate molecule and said detector molecule bound to said binding partner.

The invention also provides a method for determining kinase activity of a substrate molecule comprising:

a) phosphorylating a substrate molecule that is labelled with an energy donor with a kinase;

b) contacting the phosphorylated substrate molecule obtained in step b) with
   i) a binding partner that only binds phosphorylated substrate molecule and ii) a detection molecule, wherein the detection molecule is labelled with an energy acceptor, such that the contacting of said substrate molecule with said binding partner and said detection molecule binds said detection molecule to said binding partner; and c) determining kinase activity by measuring energy transfer from the energy donor of said substrate molecule to the energy acceptor of said detection molecule bound to said binding partner, wherein the energy donor has an emission lifetime of less than 10 microseconds wherein the energy donor is a Ru-luminophore and the energy acceptor is a fluorophore exhibiting a spectral overlap with the Ru-complexes yielding an Ro of at least 10 angstroms The invention also provides a method for determining kinase activity of a substrate molecule comprising:

a) phosphorylating a substrate molecule that is labelled with an energy acceptor with a kinase;

b) contacting the phosphorylated substrate molecule obtained in step b) with i) a binding partner that only binds phosphorylated substrate molecule and ii) a detection molecule, wherein the detection molecule is labelled with an energy donor, such that the contacting of said substrate molecule with said binding partner and said detection molecule binds said detection molecule to said binding partner; and c) determining kinase activity by measuring energy transfer from the energy donor of said detection molecule bound to said binding partner to the energy acceptor of said substrate molecule, wherein the energy donor has an emission lifetime of less than 10 microseconds wherein the energy donor is a Ru-luminophore and the energy acceptor is a fluorophore exhibiting a spectral overlap with the Ru-complexes yielding an Ro of at least 10 angstroms The invention also provides a method for determining phosphatase activity of a substrate molecule comprising a) dephosphorylating a phosphorylated substrate molecule that is labelled with an energy donor with a phosphatase;

b) contacting the dephosphorylated substrate molecule obtained in step a) with i) a binding partner that only binds phosphorylated substrate molecule and ii) a detection molecule, wherein said detection molecule is labeled with an energy acceptor, such that the contacting of said substrate molecule with said binding partner and said detection molecule binds said detection molecule to said binding partner; and c) determining phosphatase activity by measuring energy transfer from the energy donor of said substrate molecule to the energy acceptor of said detection molecule bound to said binding partner, wherein the energy donor has an emission lifetime of less than 10 microseconds wherein the energy donor is a Ru-luminophore and the energy acceptor is a fluorophore exhibiting a spectral overlap with the Ru-complexes yielding an Ro of at least 10 angstroms.

The invention also provides wherein a method for determining kinase activity of a substrate molecule comprising a) dephosphorylating a phosphorylated substrate molecule that is labelled with an energy acceptor with a phosphatase;

b) contacting the dephosphorylated substrate molecule obtained in step a) with i) a binding partner that only binds phosphorylated substrate molecule and ii) a detection molecule, wherein said detection molecule is labeled with an energy donor, such that the contacting of said substrate molecule with said binding partner and said detection molecule binds said detection molecule to said binding partner; and c) determining phosphatase activity by measuring energy transfer from the energy donor of said detection molecule bound to said binding partner to the energy acceptor of said substrate molecule, wherein the energy donor has an emission lifetime of less than 10 microseconds the energy donor is a Ru-luminophore and the energy acceptor is a fluorophore exhibiting a spectral overlap with the Ru-complexes yielding an Ro of at least 10 angstroms.

Preferably, said binding partner are metal ions which are preferably associated with a solid phase, e.g. a bead, membrane, sample holder and surface of a microtiter plate. Any bead may be used, as long as said bead is capable of binding the phosphate of a phosphorylated protein (such that it can act as a binding partner) for example, metal ions on the solid phase support of a bead). In a most preferred embodiment, said binding partner are metal ions on IMAP™ beads. Examples of suitable metal ions include iron, aluminum etc., specifically Fe(III) and AR (III). IMAP™ beads may be obtained from Molecular Devices Corp. It has been shown that IMAP™ beads can be used as binding platform to bring two fluorophores close enough together for fluorescence resonance energy transfer (FRET) being thus a universal detection system for kinase assays and phosphatase assays.

In another preferred embodiment, the substrate molecule is a protein or a peptide (polypeptide).

In comparison to a fluorescence polarization readout, an implementation with TR-FRET as readout offers the following advantages:

Increased quality of the assay signal which is expressed by the statistical parameter z', in particular for low substrate turnover.

Increased robustness of the assay signal vs. interferences of background fluorescence due to the time gated, delayed detection.

Increased sensitivity with respect to amount of substrate which needs to be converted (the FP readout measures the average signal of the fluorophores for all substrate molecules in the solution; the FRET sees only the fraction of the fluorophores bound to the phosphorylated substrate molecules).

Reduced reagent consumption by a factor of more than 20 fold.

In addition, the three parts system used in the method of the present invention has the following advantages over the two parts system of the prior art even if the latter is also implemented by (TR)-FRET:

The amount of beads needed for best binding of the substrate product and the amount of detection molecule for best energy transfer signal can be titrated separately.

The energy transfer between the detection molecule and the substrate molecule which are both bound to the bead surface leads to a more efficient FRET signal.

Furthermore, it is possible to select beads (BP), detection molecule and substrate molecule separately i.e. for example an assay toolbox which contains several universal items such as beads, detection molecules, substrates and sets of FRET pairs. Selection from this toolbox by one skilled in the art would of each bead, molecule etc. would result in different assay applications. Such flexibility and universality would be inherently difficult and practically even impossible for a two part system.

Thus, a kit for performing the method according hereinbefore and hereinafter described is also provided, comprising, in separate containers, beads, more than one detection molecule, more than one substrate molecule, wherein said detection molecules and said substrate molecule are provided as sets of FRET pairs.

Preferably, the energy donor has an emission lifetime less than 50 microsecs, more preferably less than 10 microsecs, even more preferably less than 5 microsecs. Most preferably, the energy donor has a emission lifetime of 2 to 3 microsecs.

In a preferred embodiment, a Ru-luminophore is used as energy donor. Compared to the Lanthanide (Eu, Tb, Sm) chelates and cryptates, the Ru-luminophore has several general advantages Broad emission spectrum with good overlap with acceptor, unlike the peaked spectrum of lanthanide dyes.

Higher chemical stability which is of advantage for the labeling chemistry (more harsh conditions possible, also during purification) and assays (no interference from reagent, Lanthanide dyes are known to be sensitive to important ingredients of typical kinase assays such as EDTA, Mg-ions or Mn-ions).

In another preferred embodiment, a Tb-luminophore is used as energy donor.

A particular advantage is given by the microsecond lifetime of the excited state and the resulting emission. The typical emission lifetime of the Ru(batho)$_2$bpy-complex under assay conditions is 2-3 µs. This microsecond lifetime allows efficient background suppression against fluorescence from other assay ingredients and fluorescent compounds. However, the photon emission time is 100× faster than for the lanthanides i.e. the detector integrates 100× less of its electronic background signal.

In one embodiment of the present invention, the method is performed with a system wherein the sample moves with respect to the optical detection pathway. Preferably, said system is a labware spin system, more preferably a Tecan LABCD™ or the system from SPIN-X™. In another preferred embodiment, said system is a microfluidic system or a flow through cell. In such a setting, the lanthanide emission is too slow to allow readout during the movement of the sample. In order to make use of the TR-FRET readout, the labware/disk or the sample flow, respectively, would have to go through start-stop cycles, which is practically impossible and time consuming. Alternatively one would have to modify the instrument to have a different excitation/detection path where the positions of the pathways would have to be adjusted according to the timing of the readout.

The "Fast-TR-FRET" (Fast-Time Resolved-Fluorescence resonance energy transfer) with Ru-complexes and short microsecond lifetimes allows online readout while the sample is moving without major modification and offers an unique advantage over FRET.

The IMAP™ technology is a universal assay for kinases and therefore preferably used. The FP readout, however, has the disadvantages mentioned above. The lanthanide TR-FRET cannot be readily used in such a setting.

In a preferred embodiment, the energy acceptor is a fluorophore exhibiting a spectral overlap with the Ru-complexes which yields an R$_0$ (Förster Radius) of at least 10 Å, preferably at least 20 Å, more preferably at least 50 Å. The relation between R$_0$ and the spectral overlap J(λ) is defined by the following formulae (from: Lakowicz, J. R., Principles of Fluorescence Spectroscopy, 2$^{nd}$ ed. Kluwer Academin/Plenum Publishers, p. 369):

$$R_0 = 0.211[\kappa^2 n^{-4} Q_D J(\lambda)]^{1/5} \text{ (in Å)}$$

wherein $$J(\lambda) = \int_0^\infty F_D(\lambda)\varepsilon_A(\lambda)\lambda^4 \, d\lambda = \frac{\int_0^\infty F_D(\lambda)\varepsilon_A(\lambda)\lambda^4 \, d\lambda}{\int_0^\infty F_D(\lambda) \, d\lambda}$$

In a more preferred embodiment, the energy acceptor is Alexa Fluor 700™, Atto 700™ (Atto-Tec), Dy701™ (dyamid, e.g. C$_{39}$H$_{43}$N$_2$O$_9$S$_2$Na (as a carboxylic acid)) or Alexa Fluor 750™. In a most preferred embodiment, said energy acceptor is Alexa Fluor 700™. The Alexa fluorescent dyes are trademarks of Invitrogen-Molecular Probes and generally are synthesized through sulfonation of amino-coumarin or rhomadine and may be obtained from e.g., Invitrogen.

In a most preferred embodiment, the Ru-luminophore is Ru(batho)$_2$bpy.

Additional dye pairs for such fluorescence resonance energy transfer measurements between Ru-complexes and fluorophores which can be used in the present invention are disclosed in WO02/41001, which is hereby incorporated by reference in its entirety.

The dilution of the binding partner with respect to the original IMAP bead suspension is at least 400 fold, preferably at least 1000 fold or between 400-500 fold or 1000 fold and 10,000 fold, wherein the dilution is between 2000 fold and 10,000 fold or between 2000 fold and 8000 fold. More preferably, the binding partner is diluted at about 400 fold to about 10,000 fold.

In the following section a non-limiting embodiment disclosed in the examples is discussed:

As a test system phosphorylated and unphosphorylated substrate peptide was labeled with Alexa Fluor 700™ as energy acceptor and phosphorylated substrate peptide was labeled with Ru(batho)$_2$bpy as energy donor. The Alexa labeled kinase substrate peptide is phosphorylated by the enzyme. For the detection a phosphorylated Ru(batho)$_2$bpy detection peptide and IMAP™ beads are added to the reaction mixture. Both phosphorylated substrate and detection peptides bind to the beads, and thus come into close proximity so that fluorescence resonance energy transfer (FRET) can occur (FIG. 1).

As FRET pair the long lifetime metal-ligand complex Ru(batho)$_2$bpy (τ=3 µs) was used as energy donor and Alexa Fluor 700™ as energy acceptor. Binding of the Ru labeled peptide to the IMAP™ beads did not influence the fluorescence polarization measurements with Alexa Fluor 700™ as fluorophore. In a comparison of both readout techniques (FP and FRET) FRET was proven to be the more sensitive method. Already 10% phosphorylation gives a z' factor above 0.5. Furthermore, for FRET measurements at least ten times less IMAP™ beads are needed as compared to FP. Thus, a significant reduction of reagent consumption is achieved without the necessity of miniaturized liquid handling and readout which is typically done to save costly reagents but complicates the assay handling and thereby may lead to unstable and irreproducible processing.

Summarized, the Fast-TR FRET kinase IMAP™ assay disclosed herein is robust, sensitive, needs less IMAP™ beads and has low background fluorescence because of the time gated detection.

As known from FP experiments the signal is affected by ATP because free binding sites on the beads are occupied by ATP preventing the phosphorylated peptide to bind. In contrast to ATP, EDTA had no effect on the FRET signal. The effect of ATP could be neglected after titration of the assay components of the herein described three parts system.

In principle both fluorophores could be used as labels for the substrate. Advantages of the Ru complex as substrate label are the high chemical stability and—as compared to Alexa Fluor 700—its availability as NHS ester and maleimide which enhances the flexibility of the labeling process.

An alternative to Alexa Fluor 700™ may be Atto 700™ which has comparable excitation and emission spectra and is available as NHS ester and maleimide. Due to its smaller absorption coefficient ($\epsilon=120000\,M^{-1}\,cm^{-1}$) $R_0$ is reduced by ~5 Å for the FRET pair Ru-Atto 700 compared to Ru-Alexa Fluor 700 ($\epsilon=192000\,M^{-1}\,cm^{-1}$, $R_0=62$ Å). Phosphotyrosine, other phosphorylated amino acids or other small molecules carrying a phosphate group, which are labeled with the Ru complex (or alternatively Alexa Fluor 700™ or Atto 700™) may be used as a "universal" detection molecule.

EXAMPLES

The following examples are provided for illustrating purposes and are not intended to limit the scope of applicants' invention.

Example 1

Observation of FRET due to Binding to IMAP beads

Figure 2:
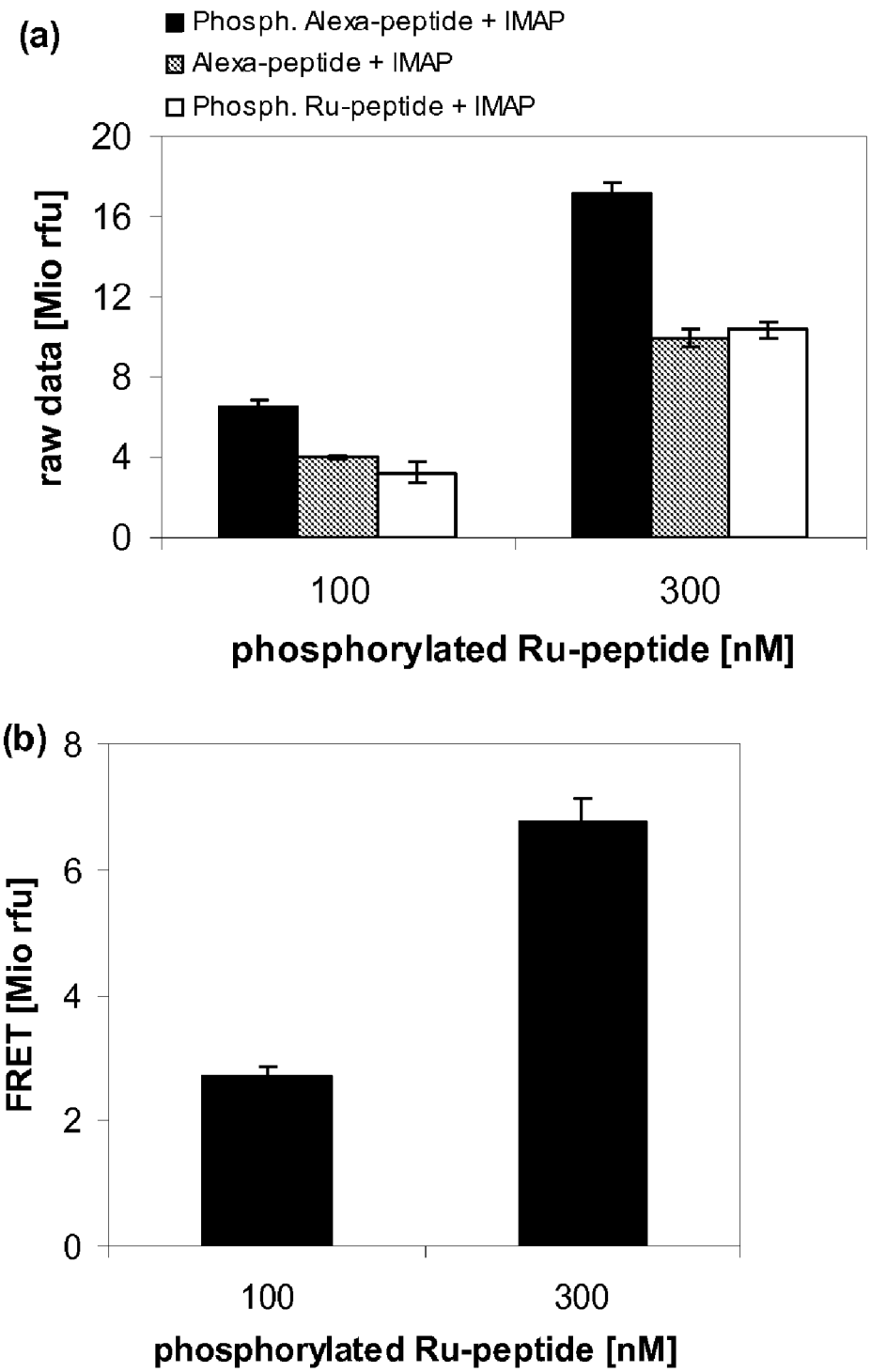
FIG. 2: Observed FRET signal (black) with 15 nM phosphorylated Alexa-peptide and 100 nM and 300 nM phosphorylated Ru-peptide, respectively, IMAP™ dilution: 1:800. Grey: 15 nM Alexa-peptide and phosphorylated Ru-peptide and IMAP™ beads, white: phosphorylated Ru-peptide and IMAP™ beads. The beads were incubated at RT for 30 minutes. Readout: 730 (30) nm, delay 100 ns, gate 100 ns, exposure time 4 s. The part (a) on the left shows the raw data, part (b) on the right shows the effective FRET signal.

Materials:
Substrate peptide (YHGHSMSAPGVSTAC (SEQ ID NO: 1)) from Biosyntan labeled with Alexa Fluor 700
Phosphorylated substrate peptide (YHGHS($H_2PO_4$)MSAPGVSTAC (SEQ ID NO: 1)) from Biosyntan labeled with Alexa Fluor 700 and Ru(batho)$_2$bpy
Kinase enzyme: PDHK2 (recombinant pyruvate dehydrogenase kinase 2, expressed according to standard methods)
IMAP™ beads from Molecular Devices (IMAP™ Explorer Kit (IPP) Product # R8062)
Buffer: IMAP™ Binding Buffer 1:5 diluted with dest. H$_2$O+0.05% BSA Instrumentation:
Zeiss plate::vision reader
Plate: Costar 384, UV-NBS
Excitation wavelength: 355 nm
Emission filter: 730 (30) nm, 615 (10) nm In a first experiment the 1:800 diluted IMAP™ beads (recommended dilution for FP measurements 1:400) were added to a mixture of 15 nM (end concentration) phosphorylated or unphosphorylated substrate peptide labeled with Alexa Fluor 700™ (hereafter (phosphorylated) Alexa-peptide) and 100 nM and 300 nM (end concentrations) phosphorylated substrate peptide labeled with Ru(batho)$_2$bpy (hereafter phosphorylated Ru-peptide), respectively. The reaction mixture was then diluted 50 times for the readout with the IMAP™ beads and phosphorylated Ru-peptide. FIG. 2a shows the raw data of this measurement. Only the FRET signal (black) was above the background signal of the Ru complex alone (white). There was no FRET due to unspecific binding of unphosphorylated Alexa-peptide to the beads (grey). The background corrected FRET signal (FIG. 2b) was increasing with increasing phosphorylated Ru-peptide concentration indicating that with 100 nM phosphorylated Ru-peptide and 15 nM phosphorylated Alexa-peptide the IMAP™ beads were not saturated.

Example 2

Comparison of Alexa-Peptide and Ru-Peptide as Substrate

Figure 3:
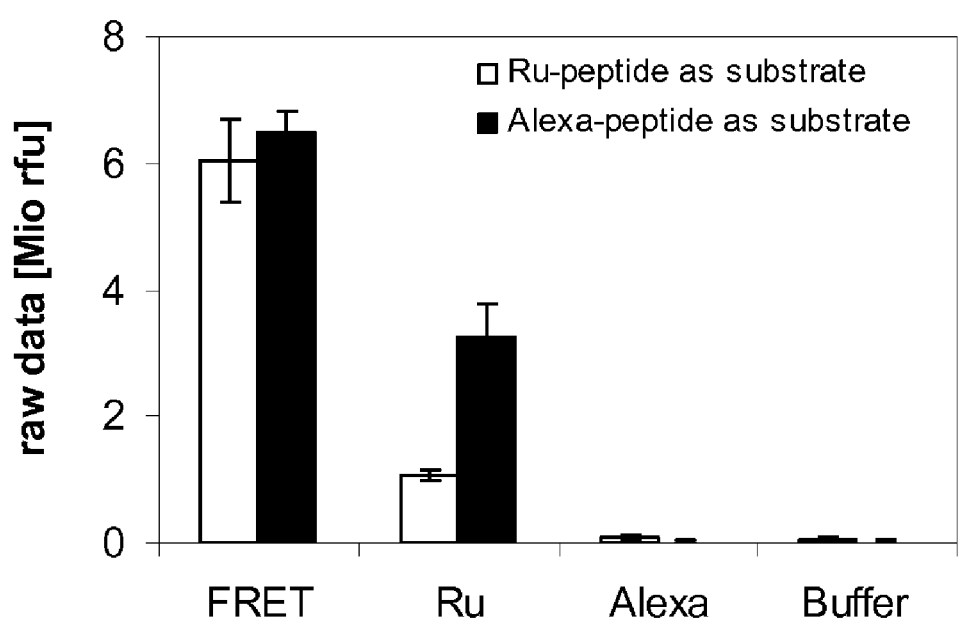
FIG. 3: Raw data of 20 nM phosphorylated Ru-peptide and 100 nM phosphorylated Alexa-peptide (IMAP™ dilution 1:4000) (white) and 15 nM phosphorylated Alexa-peptide and 100 nM Phos-PDHK-Ru (IMAP™ dilution 1:800) (black). Readout: 730 (30) nm, delay 100 ns, gate 100 ns, exposure time 10 s (white) and 4 s (black).

The experiment was also done using 20 nM phosphorylated Ru-peptide and 100 nM phosphorylated Alexa-peptide with 1:4000 diluted IMAP™ beads. FIG. 3 compares the raw data of the experiment using either Ru-peptide (white) or Alexa-peptide (black) as substrate. Because different measuring parameters were used for the two experiments, only the ratios of the FRET signal to the Ru background could be compared directly. Whereas the FRET signal was twice the Ru background when using the Alexa labeled substrate, this ratio was increased to six when using the Ru labeled substrate. In both experiments Alexa Fluor 700™ did not contribute to the background due to the time gated detection of the FRET signal (delay 100 ns).

Example 3

Titration of IMAP™ beads

Figure 4:
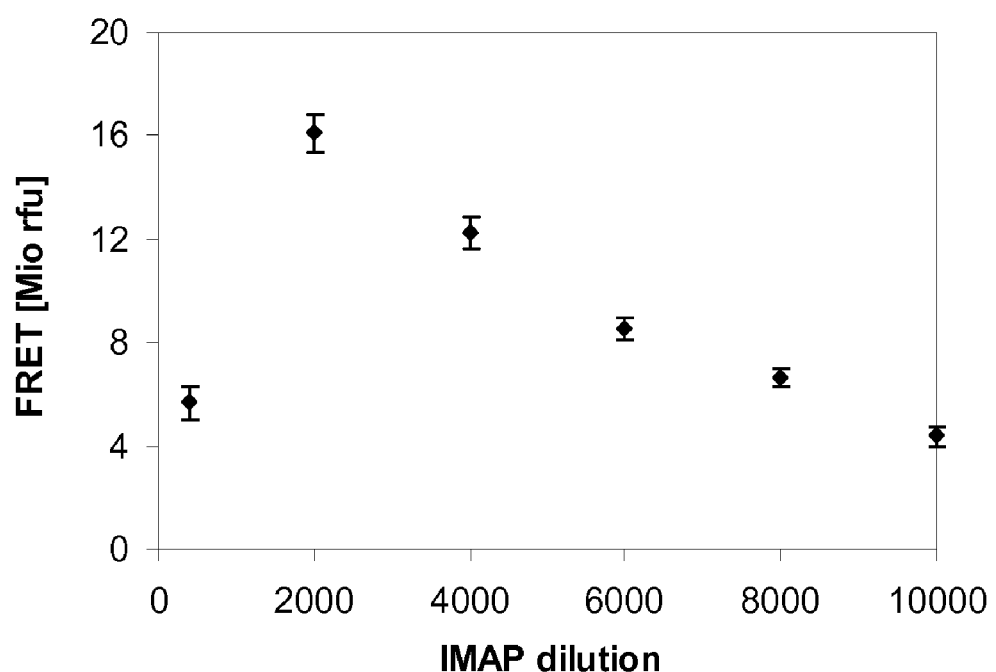
FIG. 4: FRET signal with different IMAP™ dilutions using 20 nM phosphorylated Alexa-peptide and 100 nM phosphorylated Ru-peptide, incubation 60 minutes, readout: 730 (30) nm, delay 100 ns, gate 100 ns, exposure time 5 s.

To determine optimal conditions for the readout different IMAP™ dilutions were tested with 20 nM phosphorylated Alexa-peptide and 100 nM phosphorylated Ru-peptide (FIG. 4). The FRET signal was increasing by a factor of three when diluting the IMAP™ beads 1:2000 compared to a dilution of 1:400. With further dilution the signal was decreasing again reaching about the same signal as with 1:400 with 1:10'000. As stated before, with a 1:400 dilution the IMAP™ beads were not saturated. Further dilution yielded in more phosphorylated Ru-peptide per IMAP™ bead and resulted in an increase of the FRET signal. With a dilution larger than 1:2000 the number of phosphorylated Ru-peptide per IMAP™ bead was decreased again.

Example 4

Influence of ATP and EDTA on the FRET Signal

Figure 5:
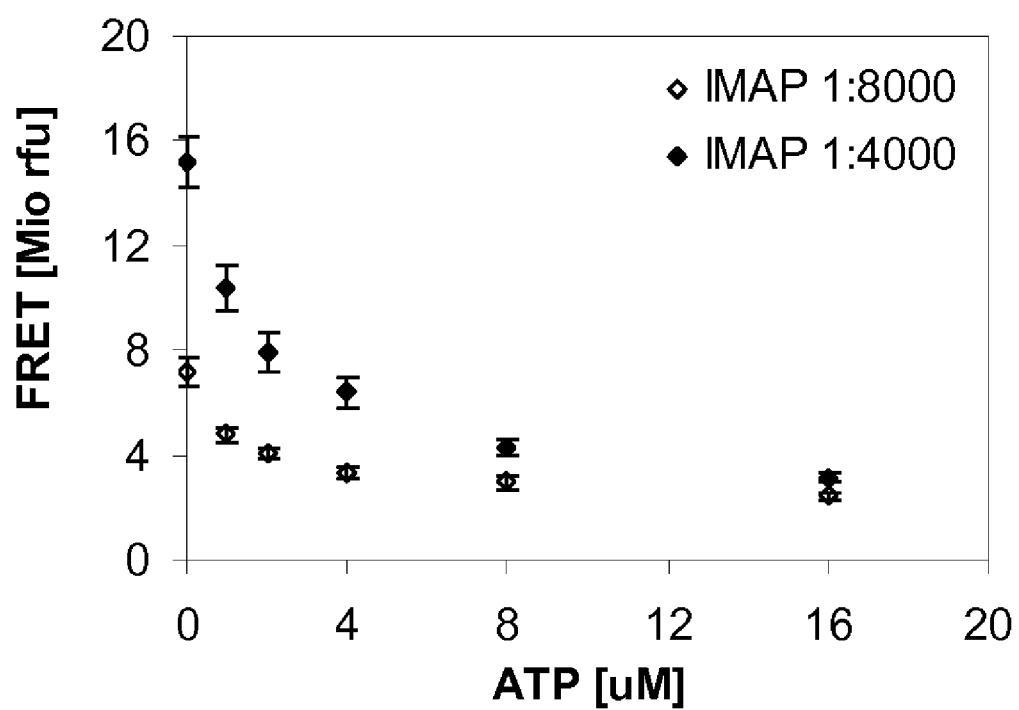
FIG. 5: Influence of ATP on the FRET signal. 20 nM phosphorylated Alexa-peptide, 100 nM phosphorylated Ru-peptide, incubation 60 minutes at RT, readout: 730 (39) nm, delay 100 ns, gate 100 ns, exposure time 8 s.

FP experiments showed that addition of ATP decreases the polarization window because ATP binds to the beads and thus prevents the phosphorylated kinase substrate to bind. Therefore ATP was expected to also influence the FRET signal. The kinase reaction was typically done with 100 μM ATP and 1 μM substrate. Before adding the IMAP™ beads for the FRET readout, the reaction mixture was diluted 50 times giving an ATP end concentration of 2 μM. FIG. 5 shows the decrease of the FRET signal with increasing ATP concentration. The FRET signal decreased by a factor of two with 2 μM ATP.

Figure 6:
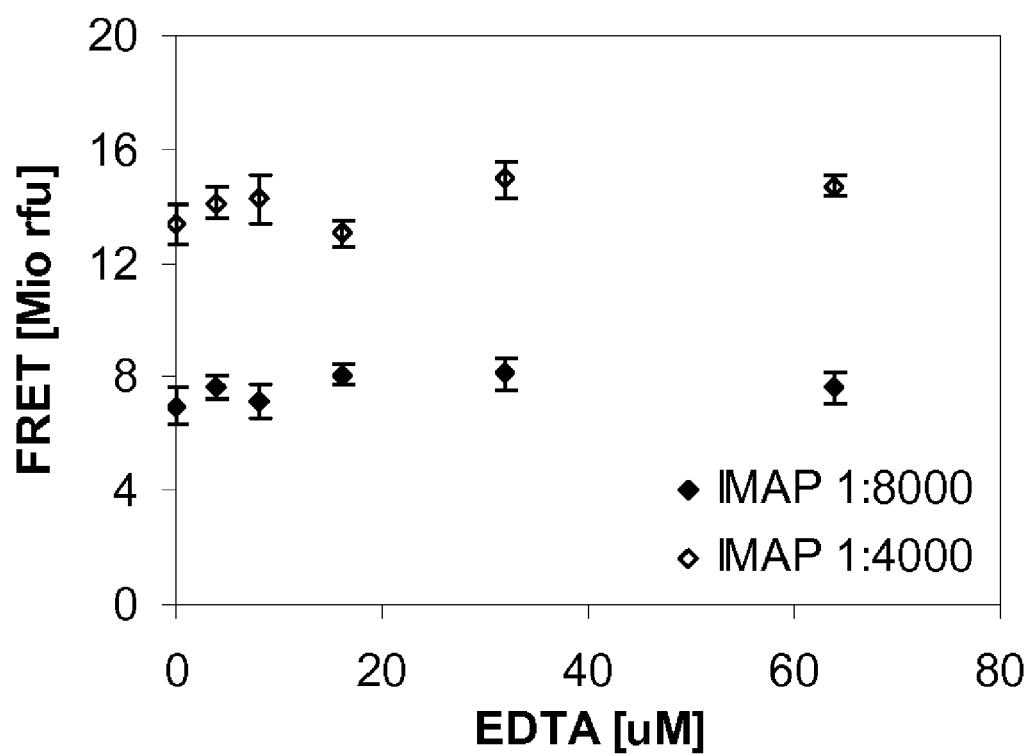
FIG. 6: Influence of EDTA on the FRET signal. 20 nM phosphorylated Alexa-peptide, 100 nM phosphorylated Ru-peptide, incubation 60 minutes at RT, readout: 730 (30) nm, delay 100 ns, gate 100 ns, exposure time 8 s.

FIG. 6 shows that the FRET signal was not influenced by addition of EDTA which was used to stop the kinase reaction. EDTA had no effect on the binding of the phosphorylated substrate to the IMAP™ bead, nor does it affect the Ruthenium complex in any way. The tested EDTA concentrations (up to 64 μM) also had no measurable influence on the IMAP™ beads. Higher concentrations may complex the $M^{3+}$ on the beads and thus influence the binding of the phosphorylated peptide.

Example 5

Kinase Assay

Figure 7:
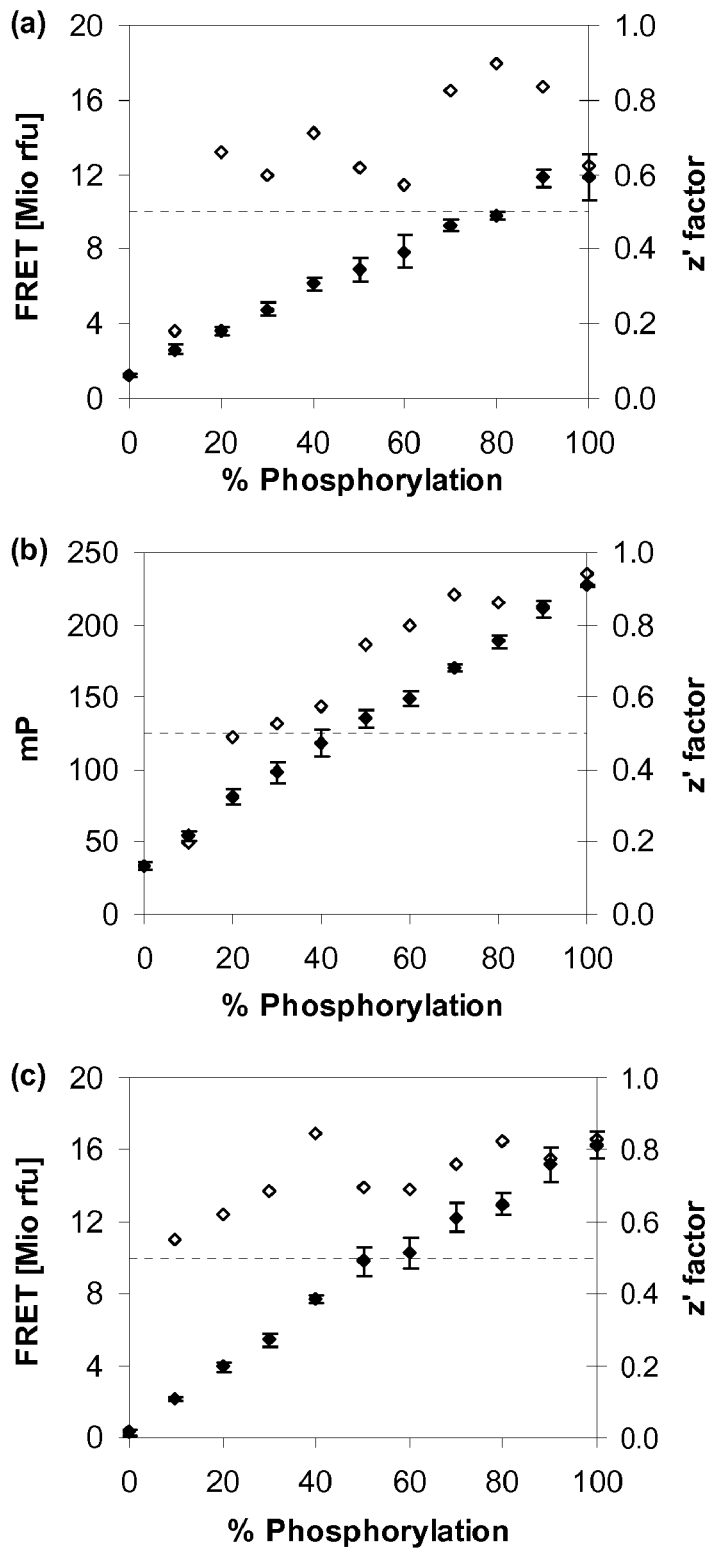
FIG. 7: Simulation of a kinase assay with 20 nM (phosphorylated) Alexa-peptide and 100 nM phosphorylated Ru-peptide, IMAP™ dilution 1:400 ((a) and (b)) and 1:4000 ((c) and (d)). Incubation 60 minutes at RT. Readout: FRET: 730 (30) nm, delay 100 ns, gate 100 ns, exposure time 10 s, FP: excitation 655 (50) nm, emission 710 (40) nm.

To test the sensitivity of the Fast-TR FRET kinase IMAP™ assay and to compare it to the established FP IMAP™ assay a simulation of the kinase assay was done. The level of phosphorylation of 20 nM Alexa-peptide was increased from 0% to 100% by mixing unphosphorylated and phosphorylated Alexa-peptides. Two IMAP dilutions were used, namely 1:400 which is the recommended dilution for FP measurements and 1:4000 which showed still a good FRET signal with 100% phosphorylated Alexa-peptide (FIG. 4). The FRET signal increased with increasing phosphorylation for both IMAP™ dilutions (FIGS. 7 (a) and (c)). As expected the FRET signal was higher for the 1:4000 dilution compared to the 1:400 dilution giving z' factors (open diamonds) larger than 0.5 from 10% to 100% phosphorylation. For the FP measurements, the detection window with an IMAP™ dilution of 1:400 was 200 mP and resulted in z' factors of 0.5 or better from 20% to 100% phosphorylation (FIG. 7 (b)). A dilution of the IMAP™ beads of 1:4000 drastically decreased the window to 70 mP (FIG. 7 (d)) and reduced the sensitivity of the FP experiment.

Example 6

Kinetic of the Kinase Reaction

Figure 8:
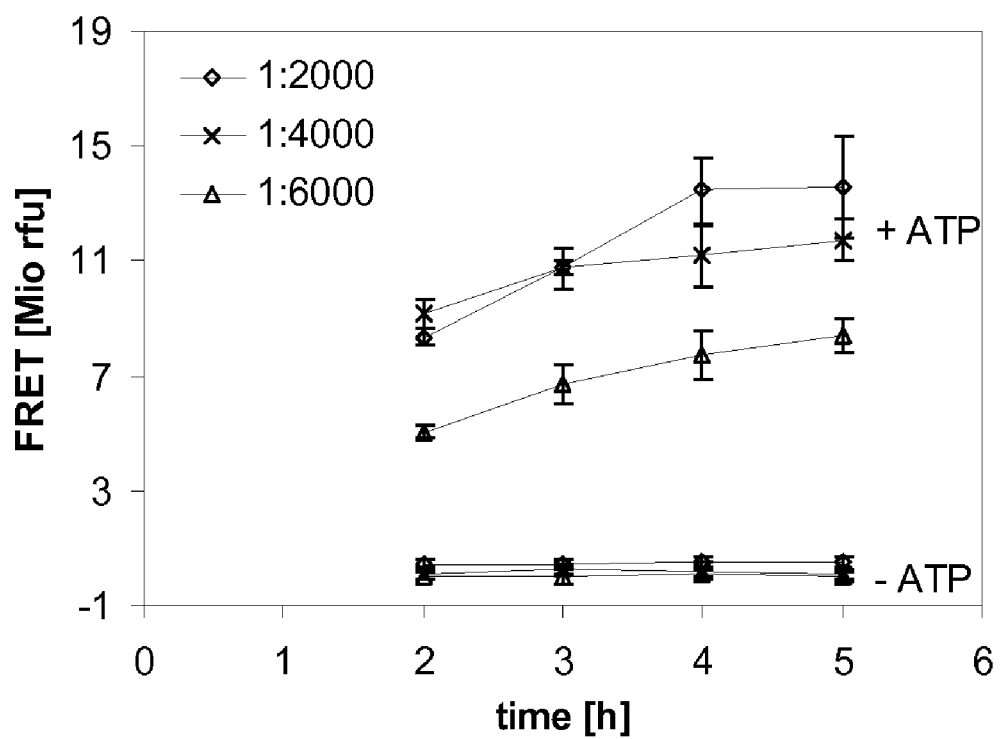
FIG. 8: Kinetic of the kinase assay. Readout: 730 (30) nm, delay 100 ns, gate 100 ns, exposure time 7 s.

1 µl of the PDHK2 enzyme was diluted in 11 µl kinase buffer (25 mM Hepes pH 7.4, 150 mM NaCl, 18.7 mM MgCl$_2$, 0.4 mM NH$_4$Ac, 0.025% Triton X-100, 1.87 mM DTT). 3 µl of a 5 µM solution of the Alexa labeled substrate-peptide in substrate buffer (25 mM Hepes pH 7.4, 150 mM NaCl, 0.01% Triton X-100) were then added to the enzyme. As a positive control the substrate solution contained 500 µM ATP whereas for the negative control no ATP was present in the reaction. This resulted in final concentrations for the reaction of 1 µM substrate and 100 µM ATP. After incubation for 2, 3, 4, and 5 hours at 30° C. the reaction was stopped by taking 1 µl of the reaction mixture and adding 24 µl of 200 nM phosphorylated Ru-peptide and 25 µl IMAP beads in IMAP binding buffer, giving a final phosphorylated Ru-peptide concentration of 100 nM. Three different dilutions of IMAP™ beads were used, 1:2000, 1:4000 and 1:8000. The beads were incubated for 60 minutes at RT. For the readout the final substrate concentration was 20 nM (phosphorylated) Alexa-peptide and with the final ATP concentration of 2 µM the FRET signal should be easily detectable (FIG. 5). FIG. 8 shows the kinetic of the kinase reaction for the positive and negative controls for the three IMAP dilutions (blue 1:2000, red 1:4000, green 1.6000). The observed FRET signal was sufficiently strong for all three dilutions.

Example 7

ATP Dependence of the Kinase Reaction

Figure 9:
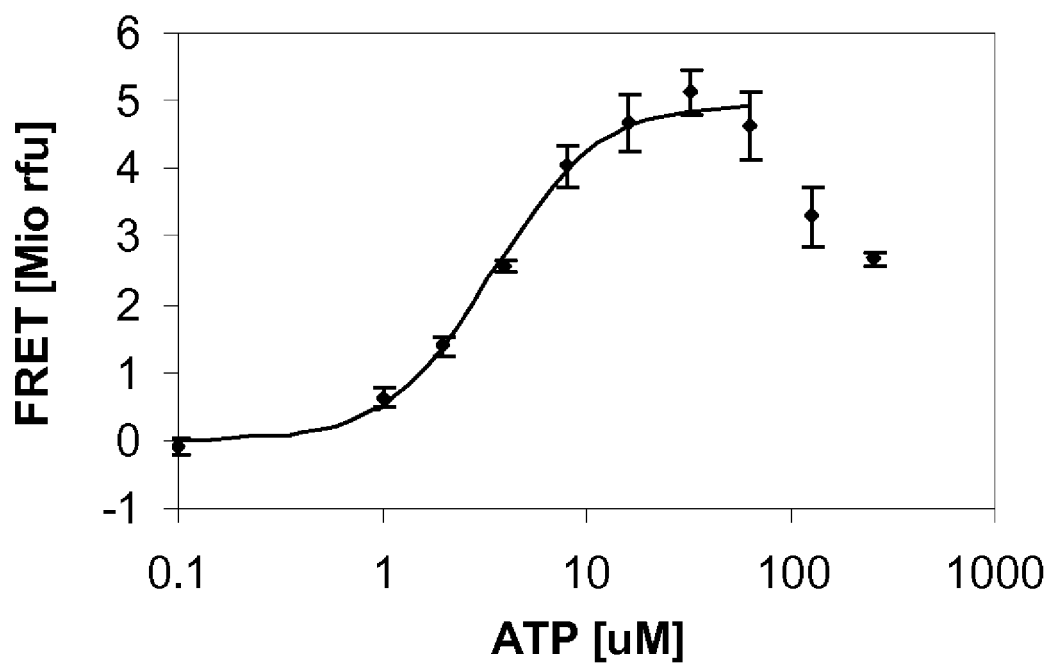
FIG. 9: Dose response curve for ATP, using 1 µM Alexa-peptide for the kinase reaction. Final concentrations in the readout were: 20 nM (phosphorylated) Alexa-peptide, 100 nM phosphorylated Ru-peptide, 1:4000 diluted IMAP™ beads. Readout: 730 (30) nm, delay 100 ns, gate 100 ns, exposure time 10 s.

The dose response curve for ATP (FIG. 9) shows that the ATP used in the assay (100 µM) was well above the EC$_{50}$ of 3.6 µM. Note that these were the concentrations in the kinase reaction, in the readout they were 50 times less. An excess of ATP prevented from finding a competitive inhibitor for the ATP binding site and assured maximal phosphorylation without inhibitor. The signal reached a maximum at 32 µM ATP. With higher ATP concentrations the signal decreased again due to free ATP in the readout mixture which bound to the IMAP™ beads and thus decreased the binding capacity of the IMAP™ beads. This problem of the binding capacity of the IMAP™ beads is well known and needs to be adjusted in the assay by proper titration of the assay reagents.

The decrease of the FRET signal due to increasing ATP concentration measured here (decrease by a factor of 1.6 and 1.9 from maximal signal (32 µM, 0.64 µM in the readout) to 128 µM (2.56 µM in the readout) and 256 µM (5.12 µM in the readout)) compared very well to the titration of ATP (FIG. 5) which resulted in a decrease of a factor of 1.6 and 2.1 for these ATP concentrations.

---

---

The invention claimed is:

1. A method for determining kinase activity comprising:
   a) providing:
      i) a substrate molecule that can be phosphorylated by a kinase wherein said substrate molecule is labeled with an energy donor of a fluorescence resonance energy transfer (FRET) pair;
      ii) a detection molecule labeled with an energy acceptor of the fluorescence resonance energy transfer (FRET) pair, and
      iii) a binding partner which binds to both the phosphorylated substrate molecule and to the detection molecule, but does not bind to the unphosphorylated substrate molecule;
   b) phosphorylating the labeled substrate molecule with a kinase;
   c) combining said labeled, phosphorylated substrate molecule, said labeled detection molecule, and said binding partner such that both of said phosphorylated substrate molecule and said detection molecule bind to said binding partner d) determining kinase activity by measuring energy transfer from the energy donor of said labeled substrate molecule to the energy acceptor of said labeled detection molecule while both are bound to said binding partner, wherein the energy donor has an emission lifetime of less than 10 microseconds.

2. A method for determining kinase activity comprising:
a) providing:
i) a substrate molecule that can be phosphorylated by a kinase wherein said substrate molecule is labeled with an energy acceptor of a fluorescence resonance energy transfer (FRET) pair;
ii) a detection molecule labeled with an energy donor of the fluorescence resonance energy transfer (FRET) pair, and
iii) a binding partner which binds to both the phosphorylated substrate molecule and to the detection molecule, but does not bind to the unphosphorylated substrate molecule;
b) phosphorylating the labeled substrate molecule with a kinase;
c) combining said labeled, phosphorylated substrate molecule, said labeled detection molecule, and said binding partner such that both of said phosphorylated substrate molecule and said detection molecule bind to said binding partner
d) determining kinase activity by measuring energy transfer from the energy donor of said labeled detection molecule to the energy acceptor of said labeled substrate molecule while both are bound to said binding partner, wherein the energy donor has an emission lifetime of less than 10 microseconds.

3. The method of claim 1 or 2, wherein the energy donor is a Ru-luminophore and the energy acceptor is a fluorophore exhibiting a spectral overlap with the Ru-complexes yielding an Ro of at least 10 angstroms.

4. A method for determining phosphatase activity comprising:
a) providing:
i) a phosphorylated substrate molecule that can be dephosphorylated by a phosphatase wherein said substrate molecule is labeled with an energy donor of a fluorescence resonance energy transfer (FRET) pair;
ii) a detection molecule labeled with an energy acceptor of the fluorescence resonance energy transfer (FRET) pair, and
iii) a binding partner which binds to both the phosphorylated substrate molecule and to the detection molecule, but does not bind to the unphosphorylated substrate molecule;

b) combining said labeled, phosphorylated substrate molecule, said labeled detection molecule, and said binding partner such that both of said detection molecule and said phosphorylated substrate molecule bind to said binding partner but not the dephosphorylated substrate molecule;
c) dephosphorylating the labeled substrate molecule with a phosphatase;
d) determining phosphatase activity by measuring the decrease in energy transfer from the energy donor of said labeled, phosphorylated substrate molecule to the energy acceptor of said labeled detection molecule resulting from the unbinding of the dephosphorylated substrate from the binding partner, wherein the energy donor has an emission lifetime of less than 10 microseconds.

5. A method for determining phosphatase activity comprising:
a) providing:
i) a phosphorylated substrate molecule that can be dephosphorylated by a phosphatase wherein said substrate molecule is labeled with an energy acceptor of a fluorescence resonance energy transfer (FRET) pair;
ii) a detection molecule labeled with an energy donor of the fluorescence resonance energy transfer (FRET) pair, and
iii) a binding partner which binds to both the phosphorylated substrate molecule and to the detection molecule, but does not bind to the unphosphorylated substrate molecule;
b) combining said labeled, phosphorylated substrate molecule, said labeled detection molecule, and said binding partner such that both of said detection molecule and said phosphorylated substrate molecule bind to said binding partner but not the dephosphorylated substrate molecule;
c) dephosphorylating the labeled substrate molecule with a phosphatase;
d) determining phosphatase activity by measuring the decrease in energy transfer from the energy donor of said labeled detection molecule to the energy acceptor of said labeled, phosphorylated substrate molecule resulting from the unbinding of the dephosphorylated substrate from the binding partner, wherein the energy donor has an emission lifetime of less than 10 microseconds.

6. The method of claim 4 or 5, wherein the energy donor is a Ru-luminophore and the energy acceptor is a fluorophore exhibiting a spectral overlap with the Ru-complexes yielding an Ro of at least 10 angstroms.

* * * * *